(12) United States Patent
Nguyen et al.

(10) Patent No.: US 6,238,658 B1
(45) Date of Patent: *May 29, 2001

(54) OXIDIZING AGENT CONTAINING SEVERAL COMPONENTS AND PROCESS FOR PERMANENTLY RESHAPING THE HAIR USING THIS AGENT

(75) Inventors: Ly-Lan Nguyen, L'Hay les Roses; Anne Sabbagh, Rueil Malmaison, both of (FR)

(73) Assignee: L'Oreal S.A., Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/221,971

(22) Filed: Dec. 29, 1998

(30) Foreign Application Priority Data

Dec. 30, 1997 (FR) .................................................. 97 16718

(51) Int. Cl.⁷ ..................................................... A61K 7/09
(52) U.S. Cl. ...................... 424/70.2; 424/401; 424/70.5; 424/70.51; 8/410; 8/411
(58) Field of Search ................................ 424/70.2, 70.5, 424/70.51, 401; 8/410, 411

(56) References Cited

U.S. PATENT DOCUMENTS

| | | | |
|---|---|---|---|
| 4,749,732 | 6/1988 | Kohl et al. | 524/43 |
| 5,565,192 | * 10/1996 | Leroy et al. | 424/70.5 |
| 6,024,769 | * 2/2000 | Cotteret | 8/411 |

FOREIGN PATENT DOCUMENTS

| | | |
|---|---|---|
| 4 131 992 | 1/1993 | (DE) . |
| 0 227 994 | 7/1987 | (EP) . |
| 0 295 780 | 12/1988 | (EP) . |
| 0 356 665 | 3/1990 | (EP) . |
| 1 530 369 | 6/1968 | (FR) . |
| 2 535 730 | 5/1984 | (FR) . |
| 2 673 197 | 8/1992 | (FR) . |
| 2 730 100 | 8/1996 | (FR) . |
| 2 116 218 | 9/1983 | (GB) . |
| 2 197 352 | 5/1988 | (GB) . |
| WO 92/05674 | 4/1992 | (WO) . |
| WO 94/07844 | 4/1994 | (WO) . |

OTHER PUBLICATIONS

Kristi J. Robson et al., "Hydroxy–4–sphingenine in human epidermal ceramides", Journal of Lipid Research, vol. 35, No. 11, Nov. 1994, pp. 2060–2068.
English Language Derwent Abstract of DE 4 131 992.
English Language Derwent Abstract of EP 0 356 665.
English Language Derwent Abstract of FR 1 530 369.
English Language Derwent Abstract of FR 2 535 730.
English Language Derwent Abstract of FR 2 673 197.
English Language Derwent Abstract of FR 2 730 100.

* cited by examiner

*Primary Examiner*—Shelley A. Dodson
*Assistant Examiner*—Konata M. George
(74) *Attorney, Agent, or Firm*—Finnegan, Henderson, Farabow, Garrett & Dunner, L.L.P.

(57) ABSTRACT

The invention relates to an oxidizing agent for use in a process for permanently reshaping the hair, this agent comprising:

- a first component comprising a composition containing at least one oxidizing agent in aqueous medium,
- a second component comprising a composition containing one thickening polymer in aqueous medium, as an aqueous or oily dispersion or as a reverse emulsion, with the proviso that said thickening polymer is not quaternary hydroxyethylcellulose;

the first and the second component are mixed with each other at the time of use in order to obtain a ready-to-use oxidizing composition to be applied to the hair in order to reform the hair's disulfide linkages.

34 Claims, No Drawings

OXIDIZING AGENT CONTAINING SEVERAL COMPONENTS AND PROCESS FOR PERMANENTLY RESHAPING THE HAIR USING THIS AGENT

The invention relates to an oxidizing agent containing at least two components, comprising a first composition containing an oxidizing agent in aqueous medium, preferably, an aqueous solution, and a second composition containing a specific thickener, described hereafter. The two compositions are mixed together close to the time of use, preferably immediately before the time of use, to form a ready-to-use mixture, and the mixture is used in a process for treating the hair to permanently reshape it. The invention also relates to processes using this agent.

One technique commonly used in the cosmetics field for imposing a long-lasting shape on the hair involves reshaping the hair using a reducing agent and then an oxidizing agent.

The technique most commonly used to permanently reshape the hair involves as a first step, opening the cystine disulfide (S—S) linkages of keratin (cystine) using a composition containing a reducing agent, and then, after the hair has been treated, the hair is preferably rinsed. The second step involves reforming the said disulfide linkages, by applying to the hair, which has been placed under tension beforehand, with curlers or the like, or which has been shaped or smoothed out by other means, an oxidizing composition also known as a "fixer", so as to give the hair the desired final shape.

This technique thus makes it possible either to make the hair wavy or to straighten it or remove curls therefrom, or alternatively to make it smooth.

The new shape given to the hair by a chemical treatment is long-lasting, i.e., lasting for a few weeks, and is resistant in particular to washing with water or with shampoo. This is in contrast with techniques using styling products which lead to a temporary reshaping, such as hairsetting, such a reshaping disappearing after styling or shampooing.

The reducing compositions generally used for the first step of a permanent-waving operation contain sulfites, bisulfites or, preferably, thiols as reducing agents. Among these, preferred reducing agents are cysteine and its derivatives, cysteamine and its derivatives, thiolactic acid and thioglycolic acid and its esters, in particular glyceryl thioglycolate. Thioglycolic acid is particularly effective and constitutes the product most frequently used to reduce the disulfide linkages of keratin.

The oxidizing agents which can be used in the fixing compositions can be chosen in particular from peroxides such as an aqueous hydrogen peroxide solution, urea peroxide, bromates such as alkali metal bromates, enzymes such as peroxidases and oxidoreductases with two unpaired electrons, persalts such as perborate and persulfates, or a mixture of alkali metal bromates and a persalt.

For certain permanent-waving techniques, such as, for example, in reshaping processes without curlers, or in a hair-straightening process, it is preferable to use sufficiently thickened oxidizing agents in order to facilitate their application, to allow better localization of the product on the hair, to avoid any running of the oxidizing composition, and to allow the hair to be held in the desired position.

However, the formulation of thickened oxidizing compositions is particularly difficult because of frequent problems of instability over time. Several phenomena generally occur: a fall in viscosity of the product and/or a decrease in the oxidizing agent titer, and/or the appearance of an unpleasant odor, or all of these shortcomings at the same time, are frequently observed in particular.

If the thickening system is separated from the oxidizing agent for keratin fibers, for example in a multi-compartment system or kit, the difficulty of obtaining a uniform thickening quickly enough and easily enough after mixing is encountered.

Broadly, the invention can solve these various problems by providing an oxidizing agent containing two components, comprising a first component comprising a composition containing an oxidizing agent in aqueous solution and a second component comprising a composition containing a thickening polymer in a specific form.

The compositions of the present invention have the advantage in particular of being very easy and quick to prepare, thereby making it possible to obtain a thickened and uniform oxidizing composition almost immediately, by simple mixing the two components.

Furthermore, the oxidizing composition of the invention can have a texture which is particularly suited to all applications and in particular to applications to the hair which is not wound on curlers; since the composition is easy to apply, it does not run, and it allows the hair to be held in the desired position.

One aspect of the invention is an oxidizing composition for permanently shaping the hair comprising:
  a first component comprising at least one oxidizing agent in aqueous medium, and
  a second component comprising at least one thickening polymer in aqueous medium, said thickening polymer being in the form of an aqueous dispersion, an oily dispersion, or as a reverse emulsion, with the proviso that said thickening polymer is not quaternary hydroxyethylcellulose;
  wherein the first and second components are to be mixed with each other at the time of initiating the permanently reshaping of the hair to obtain a ready-to-use oxidizing composition.

Another aspect of the invention is a ready-to-use oxidizing composition for permanently shaping the hair formed by mixing at or close to the time of initiating said permanently shaping of the hair:
  a first component comprising at least one oxidizing agent in aqueous medium, and
  a second component comprising at least one thickening polymer in aqueous medium, said thickening polymer being in the form of an aqueous dispersion, an oily dispersion, or as a reverse emulsion, with the proviso that said thickening polymer is not quaternary hydroxyethylcellulose.

Another aspect of the invention comprises a process for permanently reshaping the hair by applying a reducing composition followed by applying a composition obtained by mixing together, at or shortly before use, the two components of the abovementioned oxidizing agent. In particular, this aspect of the invention comprises a process for permanently reshaping the hair, comprising the steps:
  applying a composition containing at least one reducing agent to wet or dry hair, before, during or after placing the hair under tension mechanically or shaping manually;
  allowing a period of time sufficient to allow the reduction of the disulfide linkages of the hair by the at least one reducing agent
  obtaining, at or close to the end of said period of time, a ready-to-use oxidizing composition for permanently shaping the hair formed by mixing:
    a first component comprising at least one oxidizing agent in aqueous medium, and a second component comprising at least one thickening polymer in aqueous medium, the thickening polymer being in the form of an aqueous dispersion, an oily dispersion, or as a reverse emulsion, with the proviso that said thickening polymer is not quaternary hydroxyethylcellulose;

applying the ready-to-use oxidizing composition thus obtained to the hair at or shortly after the end of said period of time;

leaving the ready-to-use oxidizing composition on the hair for a period of time sufficient to allow permanent reshaping; and thereafter rinsing the hair.

Another aspect of the invention involves a process for permanently reshaping the hair, comprising the steps:

applying a composition containing at least one reducing agent to wet or dry hair, before, during or after placing the hair under tension mechanically or shaping manually;

allowing a period of time sufficient to allow the reduction of the disulfide linkages of the hair by the at least one reducing agent;

after said period of time, rinsing the hair;

obtaining, at or close to the end of the rinsing, a ready-to-use oxidizing composition for permanently shaping the hair formed by mixing:

a first component comprising at least one oxidizing agent in aqueous medium, and a second component comprising at least one thickening polymer in aqueous medium, the thickening polymer being in the form of an aqueous dispersion, an oily dispersion, or as a reverse emulsion, with the proviso that said thickening polymer is not quaternary hydroxyethylcellulose;

applying the ready-to-use oxidizing composition thus obtained to the hair at the end of or shortly after the said rinsing;

leaving the ready-to-use oxidizing composition on the hair for a period of time sufficient to allow permanent reshaping; and thereafter rinsing the hair.

Other subjects of the invention will become apparent on reading the description and the examples which follow.

In one aspect, the invention provides an oxidizing agent, in accordance with the invention, for permanently reshaping the hair comprising:

(1) a first component (A) comprising a composition comprising at least one oxidizing agent in aqueous medium, and (2) a second component (B) comprising a composition comprising at least one thickening polymer in aqueous medium, the thickening polymer being in the form of an aqueous or oily dispersion or as a reverse emulsion, with the proviso that said thickening polymer is not quaternary hydroxyethylcellulose;

wherein the components (A) and (B) are to be mixed with each other at or shortly before the time of initiating said reshaping of the hair to obtain a ready-to-use oxidizing composition intended to be applied to the hair in order to reform the hair's disulfide linkages.

The oxidizing agents in the component (A) can be chosen in particular from hydrogen peroxide, preferably, aqueous hydrogen peroxide solution, urea peroxide, alkali metal bromates and persalts, such as perborates and persulfates. The oxidizing system can contain enzymes such as peroxidases and oxidoreductases with two unpaired electrons. It is particularly preferred to use hydrogen peroxide or enzymes.

The concentration of aqueous hydrogen peroxide solution can range from 1 to 10 volumes, but is preferably about 8 volumes.

The aqueous hydrogen peroxide solution can be stabilized, for example with phenacetin, acetaniline, mono- and trisodium phosphates or with 8-hydroxyquinoline sulfates.

The concentration of alkali metal bromates is from 1 to 12% and that of persalts is from 0.1 to 15% by weight relative to the total weight of the ready-to-use oxidizing composition.

The thickening polymers in the component (B) are preferably chosen from ammonium acrylate/acrylamide copolymers as a W/O reverse emulsion, such as Bozepol C sold by Hoechst;

acrylamide/2-acrylamidomethylpropanesulfonic copolymers as a reverse emulsion, such as Sepigel 305 sold by SEPPIC;

sodium acrylate/acrylamide copolymers as a reverse emulsion, such as Sepigel 901 sold by SEPPIC;

copolymers of trimethylethylammonium methacrylate chloride/acrylate, as an oily dispersion, such as Salcare SC 92 sold by Allied Colloids;

homopolymers of crosslinked ethyltrimethylammonium methacrylate chloride, as an oily dispersion, such as Salcare SC 95 sold by Allied Colloids;

hydroxypropylmethylcellulose, as an aqueous dispersion, such as AGU D 3295A sold by Hercules.

The thickening polymer is present in the composition (B) in proportions such that the ready-to-use composition resulting from mixing the components (A) and (B) has a sufficient viscosity to prevent or reduce running on the scalp and/or in order to maintain the reshaping of the hair.

The thickening polymers preferably represent from 0.1 to 30% by weight relative to the total weight of the ready-to-use composition.

The pH of the component (A) and that of the component (B) can be adjusted so as to obtain a pH of the ready-to-use composition ranging from 2 to 9 and preferably from 2.5 to 7.5.

The oxidizing agent can also contain, either in its component (A) or in its component (B), or in the ready-to-use mixture, surfactants and treating agents, such as anionic, nonionic or amphoteric agents.

The surfactants used are those commonly used in permanent-waving oxidizing compositions and can be nonionic, anionic, cationic or amphoteric. Preferred surfactants are chosen from alkyl sulfates, alkylbenzene sulfates, alkyl ether sulfates, alkyl sulfonates, quaternary ammonium salts, alkylbetaines, oxyethylenated alkylphenols, fatty acid alkanolamides, oxyethylenated fatty acid esters and nonionic surfactants of the hydroxypropyl ether family.

These surfactants are generally used in proportions such that, in the composition resulting from mixing the components (A) and (B), their maximum proportion is about 30% by weight, and preferably from 0.5 to 10% by weight, relative to the total weight of the composition.

The treating agents which can be used are volatile or non-volatile, linear or cyclic silicones or mixtures thereof, polydimethylsiloxanes, quaternized polyorganosiloxanes, those described in French patent application 2,535,730 (the disclosure of this and all other patent and technical documents cited below are specifically incorporated by reference herein), polyorganosiloxanes containing an aminoalkyl radical which are modified with alkoxycarbonylalkyl groups, as described in patent U.S. Pat. No. 4,749,732, polyorganosiloxanes such as polydimethylsiloxane/polyoxyalkyl copolymers, such as dimethicone copolyol, a polydimethylsiloxane containing stearoxy end groups (stearoxydimethicone), a polydimethylsiloxane/dialkylammonium acetate copolymer or polydimethylsiloxane/polyalkyltin copolymer described in GB-A-2,197,352, polysiloxanes organomodified with mercapto or mercaptoalkyl groups, as described in FR-B-1,530, 369 and EP-A-0,295,780, and silanes such as stearoxytrimethylsilane.

Other treating agents can also be used, such as waxes, polymers chosen from cosmetically acceptable polymers which can be cationic, anionic, nonionic or amphoteric polymers, swelling and penetrating agents which allow the efficacy of the reducing agent to be reinforced, such as dimethylisosorbitol, urea and its derivatives, pyrrolidone, n-alkylpyrrolidone, thiamorpholinone, alkyl ethers of alkylene glycol or of dialkylene glycol, such as, for example, propylene glycol monomethyl ethyl ether, dipropylene glycol monomethyl ether, $C_3$–$C_6$ alkanediols such as, for example, 1,2-propanediol, 2-imidazolidinone, and other compounds such as fatty alcohols, lanolin derivatives, ceramides and in particular ceramides themselves, the glycoceramides and psudoceramides described in particular in FR-A-95/1399 and in Downing, Journal of Lipid Research, Vol. 35, p. 2060, 1994, or in FR-A-2,673,197, EP-A-0,227, 994, WO-94/07844 and WO-92/05674, active ingredients such as pantothenic acid and panthenol, agents for preventing hair loss, antidandruff agents, suspending agents, sequestering agents, opacifiers, dyes, sunscreens, fragrances and preserving agents.

In one process in accordance with the invention
  a composition containing at least one reducing agent is applied to the wet or dry hair, before, during or after the step of placing the hair under tension by a mechanical means or shaping the hair by any manual means;
  a composition containing an oxidizing agent as defined above in aqueous medium is mixed with a composition containing a thickening polymer, as an aqueous or oily dispersion or as a reverse emulsion as defined above;
  after leaving the reducing composition on the hair for a period of time which is sufficient to allow the reduction of the disulfide linkages of the hair, and after an optional rinsing, the ready-to-use oxidizing/fixing composition containing at least one oxidizing agent is applied to the hair;
  after leaving the fixing composition on the hair for a sufficient period of time, a final rinsing is carried out.

Preferably the reducing agent is chosen from thioglycolic acid, thiolactic acid, cysteine, cysteamine, thioglycerol, glyceryl thioglycolate or one of the cosmetically acceptable salts thereof, such as, more particularly, the hydrochlorides, hydrobromides, citrates, acetates and sulfates.

The reducing agent is used in proportions which are sufficient to reduce the disulfide linkages, and preferably in proportions ranging from 1 to 25%, in particular from 3 to 25%, by weight relative to the total weight of the ready-to-use composition.

The reducing compositions can also contain alkaline agents, surfactants or treating agents as defined above.

The application of the reducing composition can be carried out before, during or after the usual step of placing the hair under tension in a shape corresponding to the desired final shape for this hair, such as curls.

The step of placing the hair under tension can be carried out by any suitable and known mechanical means, such as, for example, rollers, curlers, etc.

It is also possible to carry out the process without using equipment for placing the hair under tension, i.e. by simply applying the composition using the fingers or a comb, which allows the hair to be sculpted in order to maintain it in a desired position, such as curls, waves or spikes.

According to an optional step of the process of the invention, after applying the reducing composition, the hair can be subjected to a heat treatment by heating to a temperature of ranging from 30 to 60° C. This heating optionally allows the final degree of curliness of the hair to be adjusted.

In practice, this operation can be carried out using a hairdressing hood, a hair dryer, an infrared radiation emitter and other standard heating equipment.

Needless to say, it is also possible to work at room temperature.

The hair can then be rinsed, which is mainly done after the hair has been shaped by placing it under tension, in particular with rollers, curlers, etc.

According to a specific embodiment of the invention, it is possible not to carry out the rinsing step after reduction, in particular when the hair has been shaped by means other than mechanical means.

In general, before carrying out the rinsing or the application of the oxidizing composition, the hair onto which the reducing composition has been applied is left to stand for a few minutes, generally ranging from 2 to 30 minutes and preferably from 5 to 20 minutes, to give the reducing agent a good amount of time to act correctly on the hair.

Preferably, during this waiting period, care should be taken to ensure that the hair does not dry out completely and thus remains damp until the next step is started.

To achieve this, bonnets or protective gels can thus be used.

Before use, the component (B) defined above is mixed with the component (A) defined above.

Preferably, 1 to 99% by weight and in particular 60 to 98.5% by weight, relative to the total weight, of component (A) containing an oxidizing agent is mixed with 99 to 1% and in particular 1.5 to 40% by weight of component (B) containing a thickening polymer as an aqueous or oily dispersion or as a reverse emulsion.

After an optional rinsing, and after the step of shaping the hair, the ready-to-use composition obtained by mixing the component (A) with the component (B) is applied.

In the case where the hair has been placed under tension by a mechanical means, the mechanical means or the curlers and the like which held the hair under tension in the desired shape throughout the treatment can be removed from the hair before or after the fixing step.

The period of time for which the fixing composition is left on the hair can preferably range from 5 to 30 min, and, more preferably, from 5 to 15 min.

The examples which follow are intended to illustrate the invention without, however, limiting the scope.

EXAMPLE 1

| 1) Part A | |
| --- | --- |
| Sepigel 501 | 8 g |

(acrylamide/sodium 2-acrylamidomethylpropanesulfonate copolymer as a 40% reverse emulsion in water/isoparaffin)

| 2) Part B | |
|---|---|
| Aqueous 50% hydrogen peroxide solution | 4.8 g |
| Stabilizers | 0.2 g |
| Fragrance | 0.5 g |
| Oxyethylenated (20 EO) oleyl alcohol | 1 g |
| Citric acid qs | pH 3 |
| Demineralized water qs | 92 g |

At the time of use, part A and part B are introduced into a shaker. The mixture is shaken and a uniform white cream-gel which is ready for use is obtained immediately.

EXAMPLE 2

| Part A | |
|---|---|
| Bozepol C (Hoechst) | 6 g |

(ammonium acrylate/acrylamide copolymer (95/5) as a W/O reverse emulsion)

| Part B | |
|---|---|
| Aqueous 50% hydrogen peroxide solution | 4.8 g |
| Stabilizers | 0.2 g |
| Fragrance | 0.5 g |
| Oxyethylenated (20 EO) oleyl alcohol | 1 g |
| Citric acid qs | pH 3 |
| Demineralized water qs | 94 g |

At the time of use, part A and part B are introduced into a shaker. The mixture is shaken and a uniform white cream-gel which is ready for use is obtained immediately.

What is claimed is:

1. An oxidizing composition for permanently shaping the hair comprising:
   a first component comprising at least one oxidizing agent in aqueous medium, and
   a second component comprising at least one thickening polymer in aqueous medium, said thickening polymer being in the form of an aqueous dispersion, an oily dispersion, or as a reverse emulsion, with the proviso that said thickening polymer is not quaternary hydroxyethylcellulose;
   wherein said first and second components are to be mixed with each other at the time of initiating said permanently reshaping of the hair to obtain a ready-to-use oxidizing composition, wherein said first and second components are present in said ready-to-use oxidizing composition in an amount sufficient to form a uniform, thickened composition and to allow permanent reshaping of the hair.

2. A ready-to-use oxidizing composition for permanently shaping the hair formed by mixing at or close to the time of initiating said permanently shaping of the hair in an amount sufficient to form a uniform, thickened composition and to allow permanent reshaping of the hair:
   a first component comprising at least one oxidizing agent in aqueous medium, and
   a second component comprising at least one thickening polymer in aqueous medium, said thickening polymer being in the form of an aqueous dispersion, an oily dispersion, or as a reverse emulsion, with the proviso that said thickening polymer is not quaternary hydroxyethylcellulose.

3. The oxidizing composition of claim 1, wherein said thickening polymer is chosen from ammonium acrylate/acrylamide copolymers, acrylamide/2-acrylamidomethylpropanesulfonic copolymers, sodium acrylate/acrylamide copolymers, trimethylethylammonium methacrylate chloride/acrylate copolymers, crosslinked ethyltrimethylammonium methacrylate chloride homopolymers and hydroxypropylmethylcellulose.

4. The oxidizing composition of claim 1, wherein said at least one oxidizing agent of said first component is chosen from hydrogen peroxide, urea peroxide, alkali metal bromates, persalts, and enzymes.

5. The oxidizing composition of claim 4, wherein said persalts are chosen from perborates and persulfates.

6. The oxidizing composition of claim 4, wherein said enzymes are chosen from peroxidases and oxidoreductase with two unpaired electrons.

7. The oxidizing composition of claim 4, wherein said hydrogen peroxide is present in an amount ranging from 1 to 10 volumes.

8. The oxidizing composition of claim 7, wherein said hydrogen peroxide is present in an amount of 8 volumes.

9. The oxidizing composition of claim 4, wherein said hydrogen peroxide is stabilized with at least one stabilizer chosen from phenacetin, acetaniline, mono- and trisodium phosphates and 8-hydroxy-quinoline sulfates.

10. The oxidizing composition of claim 4, wherein at least one alkali metal bromate is present in an amount ranging from 1 to 12% by weight relative to the total weight of the oxidizing composition.

11. The oxidizing composition of claim 4, wherein at least one persalt is present in an amount ranging from 0.1 to 15% by weight relative to the total weight of the oxidizing composition.

12. The ready-to-use oxidizing composition of claim 2, wherein said at least one thickening polymer is present in proportions ranging from 0.1 to 30% by weight relative to the total weight of the ready-to-use oxidizing composition.

13. The oxidizing composition of claim 1, wherein said first component or said second component has a pH ranging from 2 to 9.

14. The oxidizing composition of claim 13, wherein said first component or said second component has a pH ranging from 2.5 to 7.5.

15. The ready-to-use oxidizing composition of claim 1, wherein said composition additionally contains at least one surfactant chosen from anionic, nonionic, cationic and amphoteric surfactants.

16. The ready-to-use oxidizing composition of claim 15, wherein said at least one surfactant is chosen from alkyl sulfates, alkylbenzene sulfates, alkyl ether sulfates, alkyl sulfonates, quaternary ammonium salts, alkylbetaines, oxyethylenated alkylphenols, fatty acid alkanolamides, oxyethylenated fatty acid esters and nonionic surfactants of the hydroxypropyl ether family.

17. The ready-to-use oxidizing composition of claim 2, wherein said ready-to-use composition additionally comprises at least one surfactant chosen from anionic, nonionic, cationic and amphoteric surfactants, and further wherein said at least one surfactant is represent in an amount of about 30% by weight relative to the total weight of the ready-to-use oxidizing composition.

18. The ready-to-use oxidizing composition of claim 2, wherein said at least one surfactant represents from 0.5 to 10% by weight relative to the total weight of the ready-to-use oxidizing composition.

19. The ready-to-use oxidizing composition of claim 2 further comprising at least one treating agent chosen from silicones, waxes, polymers, swelling agents, penetrating agents, fatty alcohols, lanolin derivatives, ceramides, active ingredients, agents for preventing hair loss, antidandruff agents, suspending agents, sequestering agents, opacifiers, dyes, silicone and non-silicone sunscreens, preserving agents and fragrances.

20. The ready-to-use oxidizing composition of claim 19, wherein said at least one treating agent is chosen from volatile and non-volatile, linear and cyclic silicones, polydimethylsiloxanes, quaternized polyorganosiloxanes, polyorganosiloxanes containing an aminoalkyl radical which are modified with alkoxycarbonylalkyl groups, polydimethylsiloxane/polyoxyalkyl copolymers, polydimethylsiloxanes containing stearoxy end groups, polydimethylsiloxane/dialkylammonium acetate copolymers, polydimethylsiloxane/polyalkyltin copolymers, polysiloxanes organomodified with mercapto groups, polysiloxanes organomodified with mercaptoalkyl groups, silanes, waxes, cosmetically acceptable polymers, swelling and penetrating agents, active ingredients, agents for preventing hair loss, antidandruff agents, suspending agents, sequestering agents, opacifiers, dyes, sunscreens, fragrances and preserving agents.

21. The oxidizing composition of claim 2, wherein said first component represents from 1 to 99% by weight relative to the total weight of the ready-to-use oxidizing composition.

22. The oxidizing composition of claim 21, wherein said first component represents from 60 to 98.5% by weight relative to the total weight of the ready-to-use oxidizing composition.

23. The oxidizing composition of claim 2, wherein said second component represents from 1 to 99% by weight relative to the total weight of the ready-to-use oxidizing composition.

24. The oxidizing composition of claim 23, wherein said second component represents from 1.5 to 40% by weight relative to the total weight of the ready-to-use oxidizing composition.

25. A process for permanently reshaping the hair, comprising the steps:
applying a composition containing at least one reducing agent to wet or dry hair, before, during or after placing the hair under tension mechanically or shaping manually;
allowing a period of time sufficient to allow the reduction of the disulfide linkages of the hair by said at least one reducing agent
obtaining, at or close to the end of said period of time, a ready-to-use oxidizing composition for permanently shaping the hair formed by mixing:
a first component comprising at least one oxidizing agent in aqueous medium, and
a second component comprising at least one thickening polymer in aqueous medium, said thickening polymer being in the form of an aqueous dispersion, an oily dispersion, or as a reverse emulsion, with the proviso that said thickening polymer is not quaternary hydroxyethylcellulose;
applying said ready-to-use oxidizing composition thus obtained to the hair at or shortly after the end of said period of time;
leaving the ready-to-use oxidizing composition on the hair for a period of time sufficient to allow permanent reshaping; and
thereafter rinsing said hair.

26. The process of claim 25, wherein said process further comprises an additional step comprising heating the hair to a temperature ranging from 30 to 60° C. after applying said at least one reducing agent.

27. The process of claim 25, wherein said period of time sufficient to allow the reduction of the disulfide linkages of the hair ranges from 2 to 30 minutes.

28. The process of claim 27, wherein said period of time sufficient to allow the reduction of the disulfide linkages of the hair ranges from 5 to 20 minutes.

29. The process of claim 25, wherein said ready-to-use oxidizing composition thus obtained has a pH ranging from 2 to 9.

30. The process of claim 29, wherein said ready-to-use oxidizing composition thus obtained has a pH ranging from 2.5 to 7.

31. The process of claim 25, wherein from 1 to 99% by weight, relative to the total weight of the ready-to-use oxidizing composition, of said first component is mixed with from 99 to 1 % by weight, relative to the total weight of the ready-to-use oxidizing composition, of said second component.

32. The process of claim 25, wherein said period of time sufficient to allow permanent reshaping by said ready-to-use oxidizing composition is from 5 to 30 minutes.

33. The process of claim 32, wherein said period of time sufficient to allow permanent reshaping by said ready-to-use oxidizing composition is from 5 to 15 minutes.

34. A process for permanently reshaping the hair, comprising the steps:
applying a composition containing at least one reducing agent to wet or dry hair, before, during or after placing the hair under tension mechanically or shaping manually;
allowing a period of time sufficient to allow the reduction of the disulfide linkages of the hair by said at least one reducing agent;
after said period of time, rinsing said hair;
obtaining, at or close to the end of said rinsing, a ready-to-use oxidizing composition for permanently shaping the hair formed by mixing:
a first component comprising at least one oxidizing agent in aqueous medium, and
a second component comprising at least one thickening polymer in aqueous medium, said thickening polymer being in the form of an aqueous dispersion, an oily dispersion, or as a reverse emulsion, with the proviso that said thickening polymer is not quaternary hydroxyethylcellulose;
applying said ready-to-use oxidizing composition thus obtained to the hair at the end of or shortly after said rinsing;
leaving the ready-to-use oxidizing composition on the hair for a period of time sufficient to allow permanent reshaping; and
thereafter rinsing said hair.

* * * * *

UNITED STATES PATENT AND TRADEMARK OFFICE
CERTIFICATE OF CORRECTION

PATENT NO. : 6,238,658 B1
DATED : May 29, 2001
INVENTOR(S) : Ly-Lan Nguyen

Page 1 of 1

It is certified that error appears in the above-identified patent and that said Letters Patent is hereby corrected as shown below:

<u>Column 8, claim 17,</u>
Line 63, "is represent" should read -- is present --.

Signed and Sealed this

Twenty-ninth Day of January, 2002

Attest:

*Attesting Officer*

JAMES E. ROGAN
*Director of the United States Patent and Trademark Office*